(12) United States Patent
Moriwaki et al.

(10) Patent No.: US 10,883,960 B2
(45) Date of Patent: Jan. 5, 2021

(54) GAS SENSOR

(71) Applicant: DENSO CORPORATION, Kariya (JP)

(72) Inventors: Junji Moriwaki, Kariya (JP); Satoshi Hino, Kariya (JP); Hirokazu Yamada, Kariya (JP)

(73) Assignee: DENSO CORPORATION, Kariya (JP)

(*) Notice: Subject to any disclaimer, the term of this patent is extended or adjusted under 35 U.S.C. 154(b) by 241 days.

(21) Appl. No.: 15/550,450

(22) PCT Filed: Jan. 25, 2016

(86) PCT No.: PCT/JP2016/051954
§ 371 (c)(1),
(2) Date: Aug. 11, 2017

(87) PCT Pub. No.: WO2016/129365
PCT Pub. Date: Aug. 18, 2016

(65) Prior Publication Data
US 2018/0031514 A1    Feb. 1, 2018

(30) Foreign Application Priority Data

Feb. 12, 2015  (JP) ................... 2015-025155
Sep. 30, 2015  (JP) ................... 2015-193987

(51) Int. Cl.
G01N 27/409 (2006.01)
G01N 27/407 (2006.01)
(Continued)

(52) U.S. Cl.
CPC ....... G01N 27/409 (2013.01); G01N 27/4067 (2013.01); G01N 27/4078 (2013.01);
(Continued)

(58) Field of Classification Search
None
See application file for complete search history.

(56) References Cited

U.S. PATENT DOCUMENTS 4,169,778 A * 10/1979 Mann ................. G01N 27/4067
204/429
4,739,645 A * 4/1988 Drbal ................. G01N 21/7703
73/1.06

(Continued)

FOREIGN PATENT DOCUMENTS

JP      63-115751       7/1988
JP      S63-115751 U    7/1988
(Continued)

*Primary Examiner* — Peter J Macchiarolo
*Assistant Examiner* — Mohammed E Keramet-Amircola
(74) *Attorney, Agent, or Firm* — Nixon & Vanderhye P.C.

(57) ABSTRACT

A gas sensor has a structure in which a sensor body is secured to a sensor-mounting member using an attachment screw. The gas sensor is capable of ensuring the stability of installation of a protective cover. The gas sensor includes the sensor body in which a sensor device is disposed and the cylindrical attachment screw disposed on an outer circumference of the sensor body to be rotatable. The gas sensor is secured to the sensor-mounting member which has an internal thread engaging the attachment screw and a bearing surface disposed on a front end side of the internal thread. The sensor body has a flange which protrudes outwardly on the front end side of the attachment screw. The flange held between the bearing surface of the sensor-mounting member and the attachment screw in the axial direction. A protective cover is secured to the attachment screw closer to the base end side than an external thread engaging the internal thread is. The protective cover covers an outer periphery of at least a portion of the sensor body which is closer to the base end side than the sensor-mounting member is.

9 Claims, 16 Drawing Sheets

(51) Int. Cl.
  *G01N 27/406*  (2006.01)
  *G01N 27/417*  (2006.01)
  *G01N 33/00*   (2006.01)
  *G01M 15/10*    (2006.01)

(52) U.S. Cl.
  CPC ....... *G01N 27/417* (2013.01); *G01N 33/0006* (2013.01); *G01M 15/104* (2013.01); *G01M 15/106* (2013.01); *G01N 33/0016* (2013.01)

(56) References Cited

U.S. PATENT DOCUMENTS

| | | |
|---|---|---|
| 5,955,656 A | 9/1999 | Graser et al. |
| 2003/0188568 A1 | 10/2003 | Kurachi et al. |
| 2004/0216513 A1 | 11/2004 | Kurachi et al. |
| 2011/0259084 A1* | 10/2011 | Atsumi .............. G01N 27/4067 73/31.05 |
| 2012/0102917 A1* | 5/2012 | Gibson .............. G01N 27/4067 60/273 |
| 2012/0255356 A1 | 10/2012 | Kume et al. |

FOREIGN PATENT DOCUMENTS

| | | | | |
|---|---|---|---|---|
| JP | 2000-234962 | | 8/2000 | |
| JP | 2004-245663 | | 9/2004 | |
| JP | 2004245663 A | * | 9/2004 | ........... G01N 27/409 |
| JP | 2010-25947 | | 2/2010 | |
| JP | 2010025947 A | * | 2/2010 | ............ G01N 27/04 |
| JP | 2010-286332 | | 12/2010 | |

* cited by examiner

FIG.13
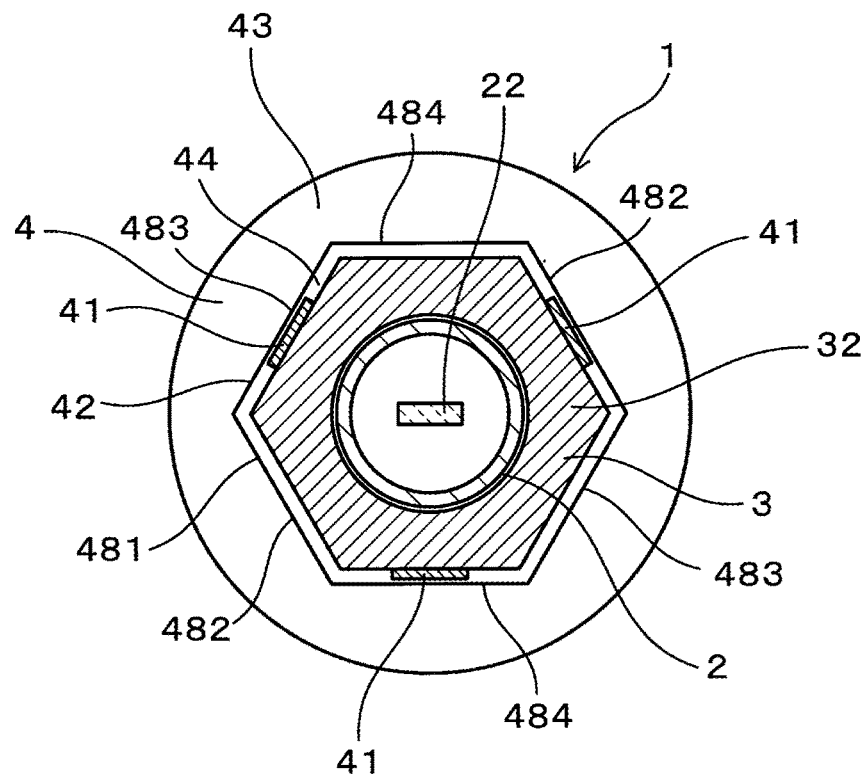
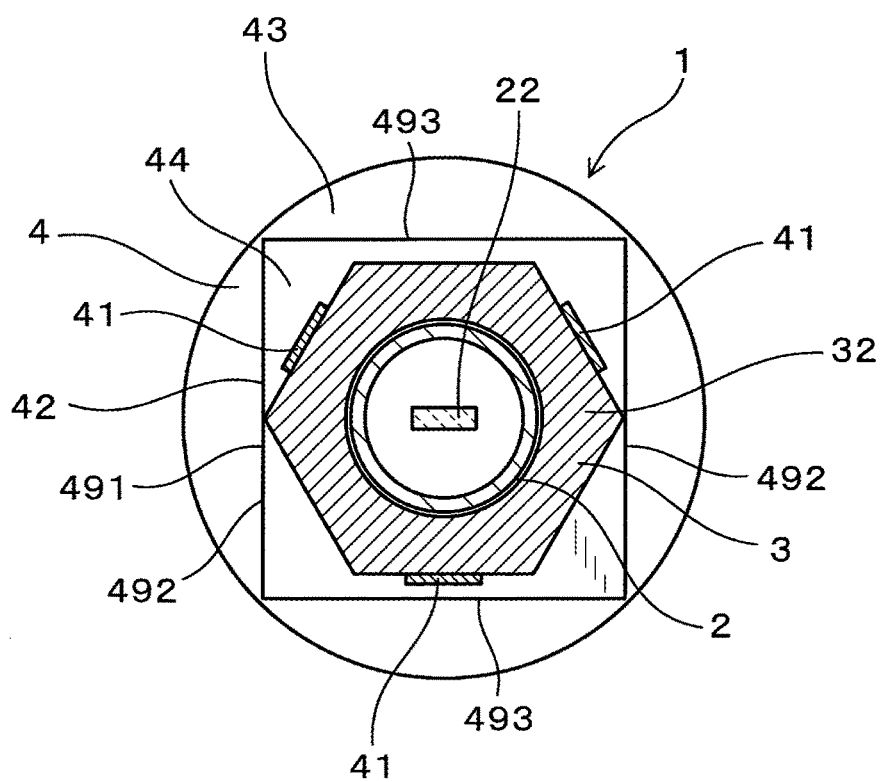
FIG.14

FIG.16
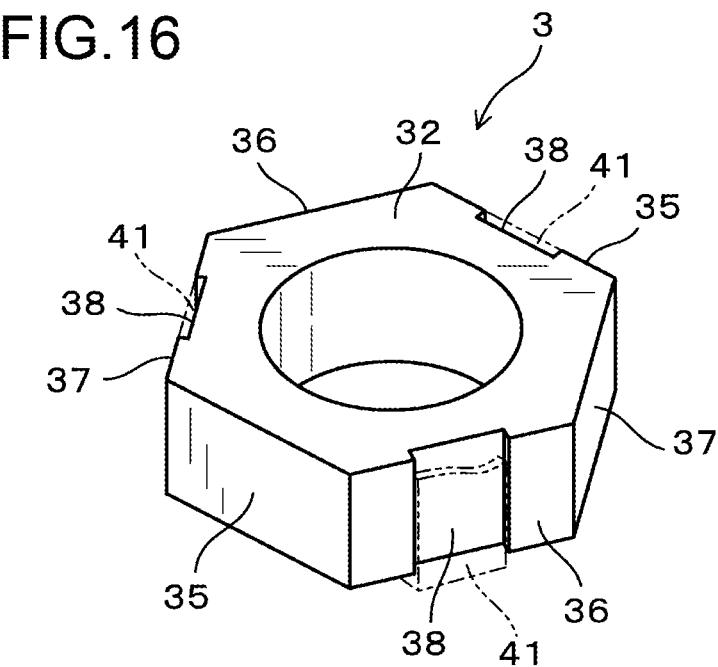
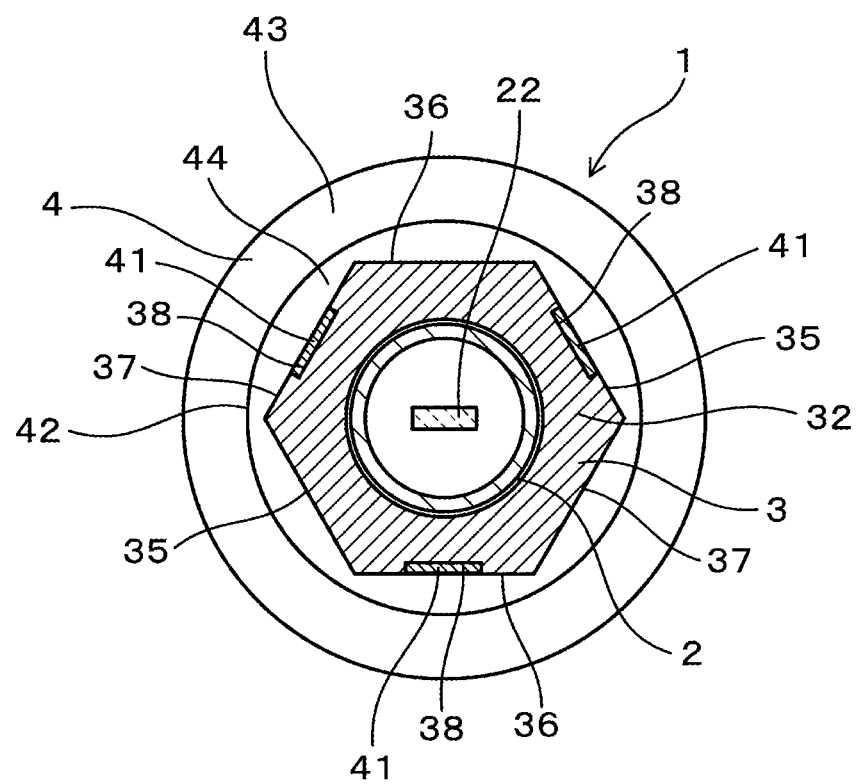
FIG.17

GAS SENSOR

CROSS-REFERENCE TO RELATED APPLICATION

This application is the U.S. national phase of International Application No. PCT/JP2016/051954 filed Jan. 25, 2016 which designated the U.S. and claims priority to JP Patent Application Nos. 2015-025155 filed Feb. 12, 2015 and 2015-193987 filed Sep. 30, 2015, the entire contents of each of which are hereby incorporated by reference.

TECHNICAL FIELD

The present invention generally relates to a gas sensor which measures the concentration of a given gas component contained in gas.

BACKGROUND ART

There are gas sensors which measure the concentration of a given gas component of gas and are used with a front end thereof disposed inside a pipe through which the gas flows. For instance, the gas sensor which measures the concentration of oxygen contained in exhaust gas emitted from an internal combustion engine of an automotive vehicle is mounted in an exhaust gas through which high-temperature exhaust gas flows. The gas sensor has leads extending outside a base end portion thereof. A sealing member made of, for example, rubber is disposed in the base end portion to hermetically seal the leads. The exhaust gas has a high temperature and thus needs to thermally protect the sealing member. In a case where the gas sensor is installed in the exhaust pipe of the engine mounted in the vehicle, it is necessary to protect the base end portion of the gas sensor from flying stones depending upon the location of installation of the gas sensor.

Japanese Patent First Publication No. 2010-286332 teaches a gas sensor which is equipped with a protective cover expanding outwardly. When the gas sensor is secured to a mounting portion (i.e., the exhaust pipe), the protective cover is held between the mounting portion and a mounting fit portion of the gas sensor on which a tool is fit which secures the gas sensor to the mounting portion.

SUMMARY OF THE INVENTION

Problem to be Solved by the Invention

However, in a case where the above protective cover is used with a gas sensor which includes a sensor body and a cylindrical attachment screw disposed on an outer circumference of the sensor body to be rotatable and is secured to the mounting portion through the attachment screw, it may be difficult to ensure the stability in securing the gas sensor to the mounting portion.

Specifically, when the protective cover is used in the gas sensor designed to have the sensor body firmly secured by the attachment screw in the axial direction thereof, it will cause the protective cover and the sensor body to be fastened to the mounting member at different portions of the attachment screw, thereby resulting in a difficulty in fixing both the protective cover and the sensor body with a required degree of power. In other words, increasing in power to fasten the protective cover will result in a decrease in power to fasten the sensor body, while increasing in power to fasten the sensor body will result in a decrease in power to fasten the protective cover.

The present invention was made in view of the above problems and is to provide a gas sensor which has a structure in which a sensor body is secured to a sensor-mounting member using an attachment screw and ensures the stability in installing a protective cover.

Means for Solving the Problem

According to one aspect of the invention, there is provided a gas sensor which comprises a sensor body in which a sensor device is disposed and a cylindrical attachment screw disposed on an outer circumference of the sensor body to be rotatable and is designed to be secured to a mounting portion equipped with an internal thread engaging the attachment screw and a bearing surface which is located on a front end side of the internal thread, characterized in that the sensor body has a flange which protrudes outwardly on a front end side of the attachment screw, the flange being designed to be retained between the bearing surface of the mounting portion and the attachment screw in an axial direction and in that a protective cover is secured to the attachment screw closer to a base end side than an external thread engaging the internal thread is and covers an outer periphery of at least a portion of the sensor body which is arranged closer to the base end side than the mounting portion is.

Beneficial Advantage

In the above gas sensor, the protective cover is fixed closer to the base end side than the external thread of the attachment screw is. This eliminates adverse effects of the protective cover on engagement between the attachment screw and the internal thread. In other words, the protective cover is not firmly retained between the attachment screw and the mounting portion in the axial direction, thereby enabling the attachment screw to be fastened to the internal thread to hold the flange of the sensor body between the attachment screw and the bearing surface of the mounting portion using a required degree of power. This ensures the stability in securing the sensor body to the sensor-mounting member and achieves the installation of the protective cover on the gas sensor.

As apparent from the above discussion, the present invention provides a gas sensor which has a structure in which a sensor body is attached to a sensor-mounting member using an attachment screw and ensures the stability of installation of a protective cover.

BRIEF DESCRIPTION OF THE DRAWINGS

FIG. 13 is a sectional view taken along the line XIII-XIII in FIG. 12.

FIG. 14 is a sectional view of an attachment screw and a protective cover in the seventh embodiment.

FIG. 16 is a perspective view which illustrates a large-diameter portion of an attachment screw in the eighth embodiment.

FIG. 17 is a sectional view taken along the line XVII-XVII in FIG. 15.

EMBODIMENT FOR CARRYING OUT THE INVENTION

First Embodiment

Figure 1:
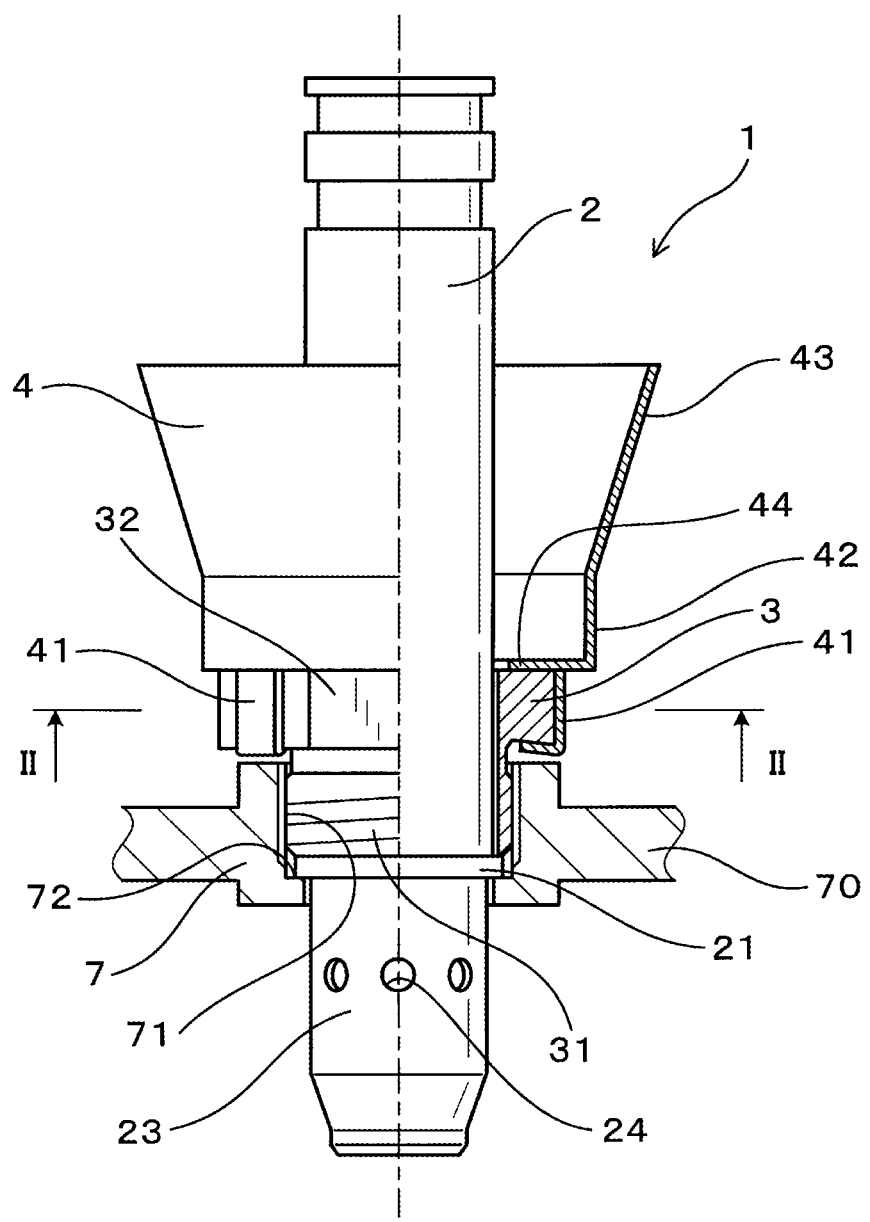
FIG. 1 is a partially sectional front view of a gas sensor installed in a mounting portion according to the first embodiment.
Figure 2:
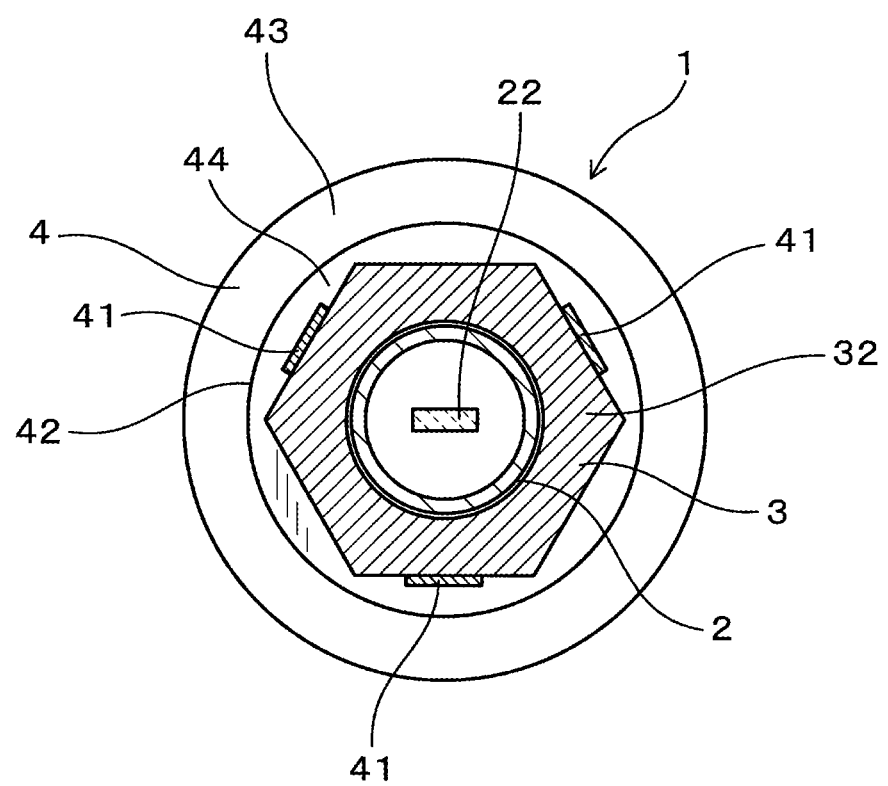
FIG. 2 is a sectional view, as taken along the line II-II in FIG. 1.

The gas sensor 1 of the first embodiment will be described below using FIGS. 1 to 6. The gas sensor 1 is, as illustrated in FIGS. 1 and 2, equipped with the sensor body 2 in which the sensor device 22 is disposed and the cylindrical attachment screw 3 which is mounted on an outer circumference of the sensor body 2 to be rotatable. The gas sensor 1 is secured to the sensor-mounting member 7 which has internal thread 71 engaging the attachment screw 3 and the bearing surface 72 located closer to the front of the gas sensor 1 than the internal thread 71 is.

Figure 3:
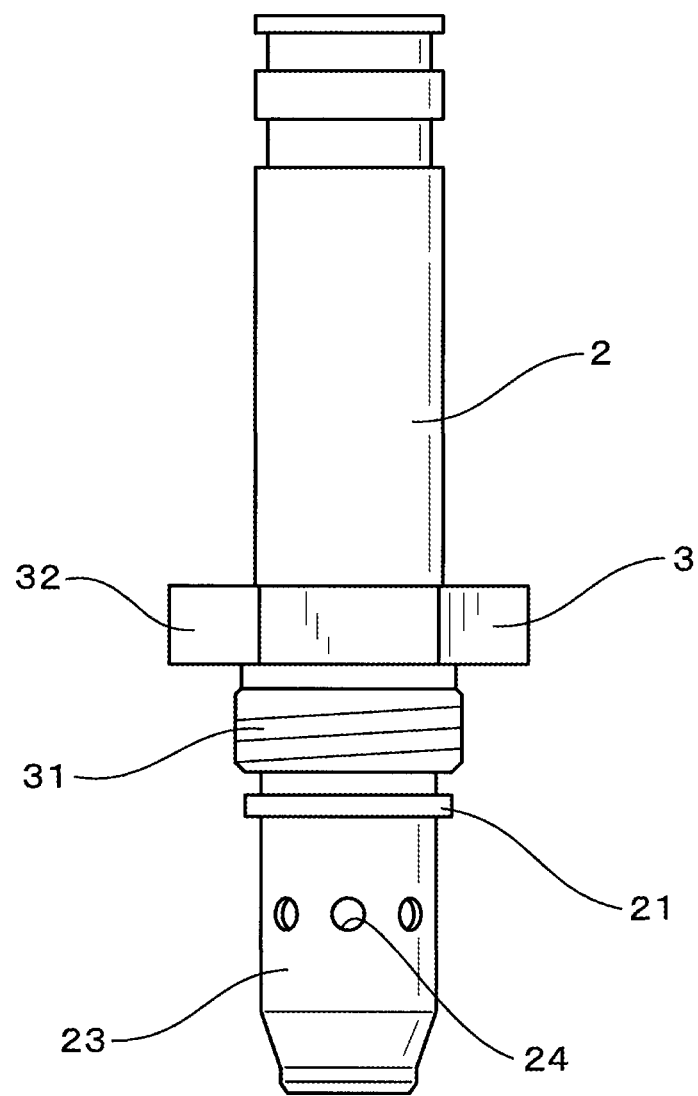
FIG. 3 is a front view which illustrates a gas sensor from which a protective cover is removed in the first embodiment.
Figure 4:
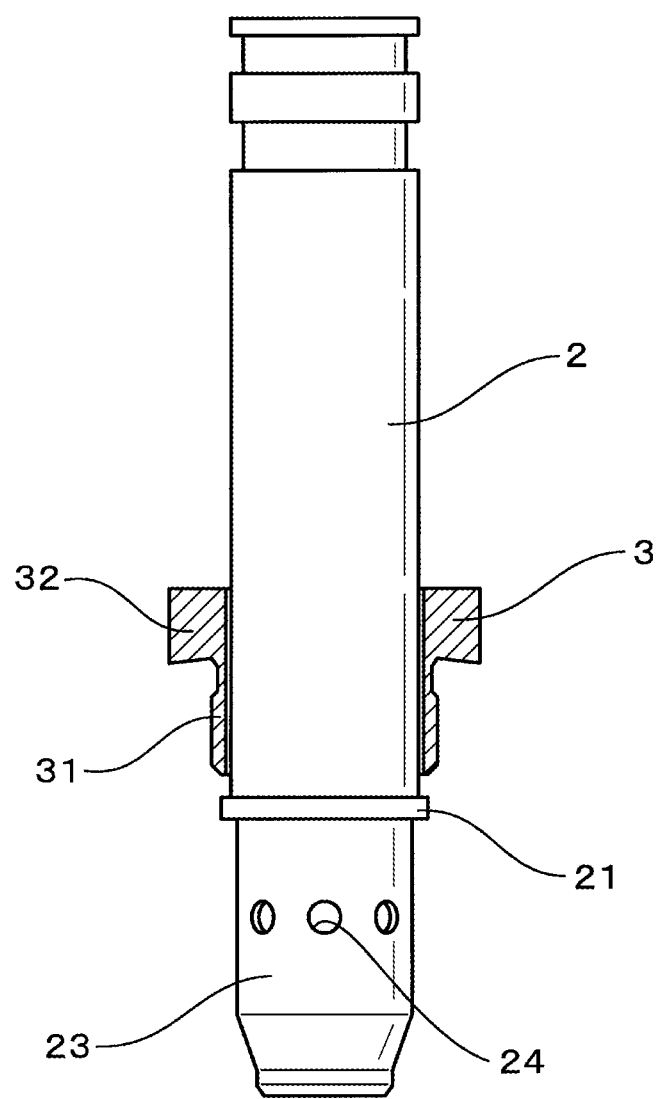
FIG. 4 is a partially sectional front view which illustrates a gas sensor on which a protective cover is not mounted in the first embodiment.

The sensor body 2, as illustrated in FIGS. 1, 3, and 4, has the flange 21 which extend outwardly from the sensor body 2 at the front end of the attachment screw 3. The flange 21 is held between the bearing surface 72 of the sensor-mounting member 7 and the attachment screw 3 in the axial direction of the gas sensor 1. The protective cover 4 is secured to the attachment screw 3 and located closer to a base end of the sensor body 2 than the external thread 31 meshing with the internal thread 71 is. The protective cover 4 covers at least a portion of an outer periphery of the sensor body 2 which is located closer to the base end of the sensor body 2 than the sensor-mounting member 7 is.

Unless otherwise specified, the axial direction represents an axial direction of the gas sensor 1. A portion of the gas sensor 1 which is inserted into a flow path of measurement gas, such as an exhaust pipe, in the axial direction will be referred to as a front end side or a front end, while an opposite portion thereof will be referred to as a base end side or a base end.

In this embodiment, the protective cover 4 is secured to the attachment screw 3 to be detachable therefrom.

The attachment screw 3 is equipped with the tool engaging portion 32 which is located closer to the base end than the external thread 31 is. The tool engaging portion 32 is formed by a large-diameter portion of the attachment screw 3 which protrudes outwardly from the sensor body 2 outside the external thread 31. The protective cover 4 are equipped with the hooks 41 which engage the tool engaging portion 32 (i.e., the large-diameter portion).

The sensor body 2, as illustrated in FIGS. 2 to 4, has the sensor device 22 disposed in the bottomed cylindrical device cover 23. The flange 21 protrudes outwardly from an outer side surface of the sensor body 2. The flange 21 is shaped in a circular form around an entire circumference of the sensor body 2. The sensor device 22 has a measuring portion disposed inside the device cover 23 which is arranged closer to the front end side than the flange 21 is. The device cover 23 has formed therein the gas holes 24 through which the measurement gas (i.e., exhaust gas) is introduced to the measuring portion.

Lead wires (not shown) which are connected to the sensor device 22 extend outside the base end of the sensor body 2. A sealing member (not shown) which hermetically seal circumferences of the lead wires is installed on the base end of the sensor body 2.

The attachment screw 3 which is arranged around the outer circumference of the sensor body 2 is loosely fit on the sensor body 2 to be rotatable in a circumferential direction of the sensor body 2. The tool engaging portion 32 that is the large-diameter portion, as can be seen in FIG. 2, has a transverse section perpendicular to the axial direction which is substantially of a regular hexagonal shape. The outline of the traverse section is shaped to have an inscribed circle whose diameter is greater than that of the external thread 31.

Figure 6:
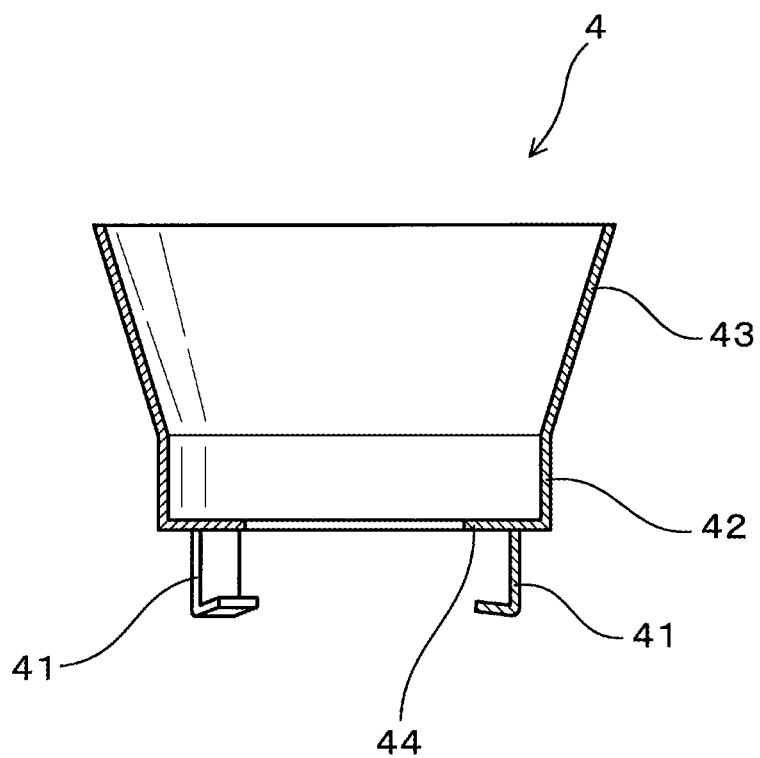
FIG. 6 is a sectional view of a protective cover in the first embodiment.

The protective cover 4, as illustrated in FIGS. 1 and 6, includes the cylindrical portion 42 which extend parallel to the axial direction, the large-diameter portion 43 whose diameter increases as approaching the base end side from a base end of the cylindrical portion 42, and the bottom plate 44 which extend from the front ends of the cylindrical portion 42 in an inward direction of the protective cover 4. The bottom plate 44 has a plurality of hooks 41 extending to the front end side. In this embodiment, the three hooks are, as can be seen in FIG. 3, formed and arranged at equal intervals away from each other in the circumferential direction of the protective cover 4. The hooks 41, as illustrated in FIG. 6, have inwardly bent end portions which are fit on the front end surface of the tool engaging portion 32 of the attachment screw 3.

The three hooks 41 are, as clearly illustrated in FIGS. 1 and 2, arranged along three of six side surfaces of the tool engaging portion 32 of the attachment screw 3, respectively. The bottom plate 44 of the protective cover 4 is in contact with the base end surface of the tool engaging portion 32. The bottom plate 44 and the hooks 41, thus, hold ends of the tool engaging portion 32 which are opposed to each other in the axial direction of the gas sensor 1, thereby attaching the protective cover 4 to the attachment screw 3.

The sensor-mounting member 7 to which the gas sensor 1 is secured is made of a boss formed on the exhaust pipe 70 of an internal combustion engine. The sensor-mounting member 7 has the internal thread 71 formed on an inner circumferential surface of a through hole extending from inside to outside the exhaust pipe 70. The sensor-mounting member 7 has a small-diameter portion which lies on the front end side of the through hole (i.e., inside the exhaust pipe 70), protrudes inwardly in the through hole, and has a base end surface (which faces outside the exhaust pipe 70) forming the bearing surface 72.

When the gas sensor 1 is secured to the sensor-mounting member 7, the protective cover 4 covers a portion of the outer periphery of the gas sensor 1 which is exposed outside the exhaust pipe 70. The protective cover 4 is interposed between the exhaust pipe 70 and the sensor body 2 to block heat from the exhaust pipe 70, thereby protecting the base end portion of the gas sensor 1. The protective cover 4 also serves as a heat dissipating fin to minimize a rise in temperature of the base end portion of the gas sensor 1. Further, the protective cover 4 also functions to protect the base end portion of the gas sensor 1 against flying stones.

The installation of the gas sensor 1 on the sensor-mounting member 7 may be achieved in the following steps.

Figure 5:
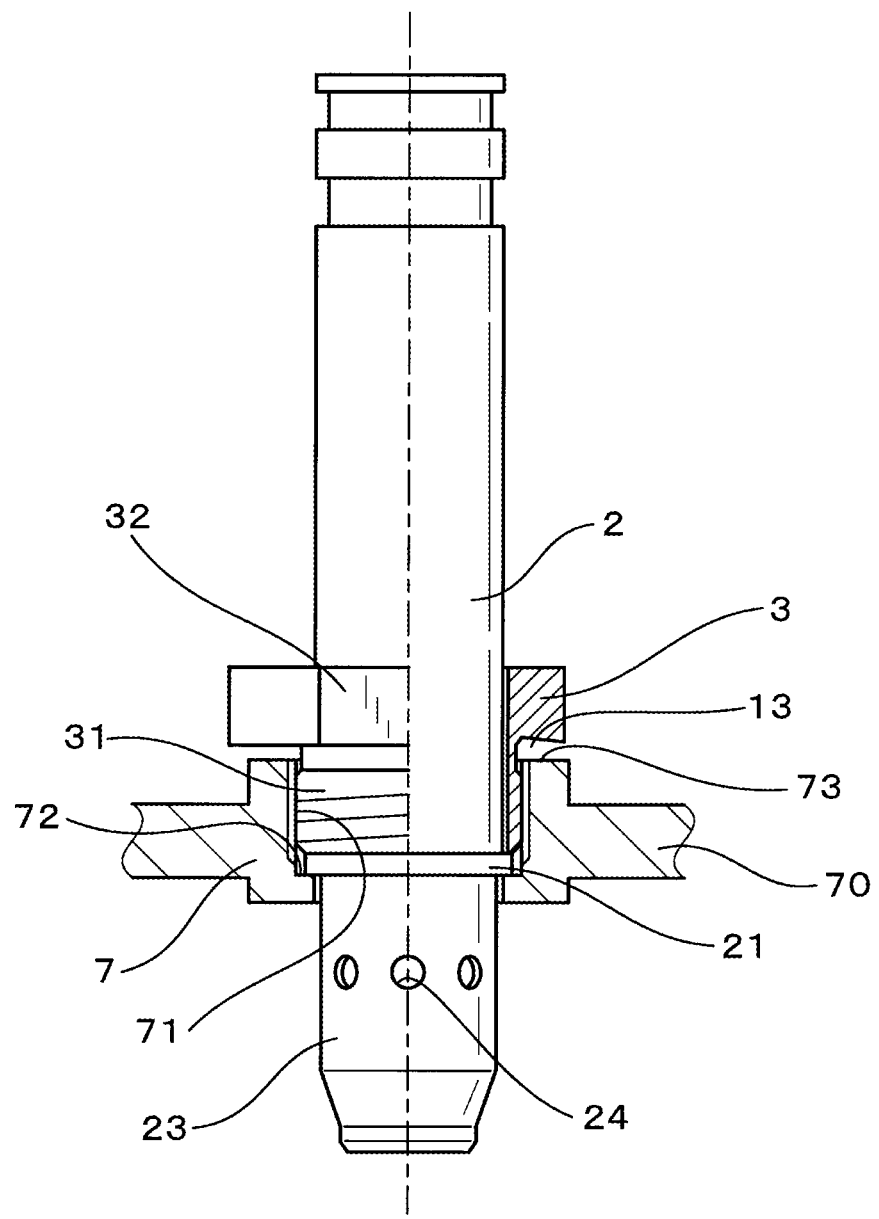
FIG. 5 is a partially sectional front view which illustrates a sensor body fixed to a mounting portion using an attachment screw.

First, the sensor body 2 before the protective cover 4 is installed, but after the attachment screw 3 is installed (see FIGS. 3 and 4) is placed in the sensor-mounting member 7. Specifically, the flange 21 of the sensor body 2 is supported by the bearing surface 72. The attachment screw 3 is tightened to achieve engagement of the external thread 31 with the internal thread 71, thereby holding the flange 21, as can be seen in FIG. 5, between the front end surface of the attachment screw 3 and the bearing surface 72 in the axial direction. This achieves firm attachment of the sensor body 2 to the sensor-mounting member 7. The air gap 13 is formed between the base end surface 73 of the sensor-mounting member 7 and the tool engaging portion 32 (i.e., the large-diameter portion) of the attachment screw 3 in the axial direction.

Subsequently, the protective cover 4 is mounted on the attachment screw 3. Specifically, the protective cover 4 is moved in the axial direction from the base end side to the front end side of the sensor body 2 so as to insert the sensor body 2 inside the protective cover 4. The hooks 41 are then slidably moved on the side surface of the tool engaging portion 32 of the attachment screw 3. It is advisable that the hooks 41 be slid on the side surface of the tool engaging portion 32 while being flexed outwardly. The hooks 41 is then, as illustrated in FIG. 1, placed in engagement with the front end surface of the tool engaging portion 32, thereby achieving firm securement of the protective cover 4 to the attachment screw 3.

The operation and beneficial advantages of this embodiment will be described below.

The gas sensor 1 has the protective cover 4 secured to a portion of the attachment screw 3 which is closer to the base end side than the external thread 31 is. This eliminates adverse effects of the protective cover 4 on screw engagement between the attachment screw 3 and the internal thread 71. In other words, the protective cover 4 is not retained between the attachment screw 3 and the sensor-mounting member 7 in the axial direction. This enables the flange 21 of the sensor body 2 to be held between the attachment screw 3 and the bearing surface 72 of the sensor-mounting member 7 by means of a strong force, as produced by threadably engaging the attachment screw 3 with the internal thread 71, thereby ensuring the stability in securing the sensor body 2 to the sensor-mounting member 7 to achieve firm attachment of the protective cover 4 to the gas sensor 1.

The protective cover 4 is designed to be detachably mounted on the attachment screw 3. This enables the protective cover 4 to be attached to only gas sensors which are required to be protected, thereby achieving shared use thereof. Usually, there are a plurality of portions of, for example, the vehicle on which gas sensors are mounted and which require or do not require the protective cover 4 for protecting the gas sensors from heat or flying stones. It is desirable to use gas sensors (i.e., sensor bodies) which have a common structure in terms of production costs or ease of installation of the gas sensors. The sensor bodies 2 or the attachment screws 3 may, therefore, be used commonly with only places on the vehicle which require the protective cover 4 by designing the protective cover 4 to be detachable, thereby enabling a gas measuring system which is equipped with a plurality of gas sensors and installed in the vehicle to be reduced in overall manufacturing cost. The above detachable structure enables the protective cover 4 to be mounted on the attachment screw 3 after the sensor body 2 is installed in the exhaust pipe. In other words, the tightening of the attachment screw 3 is completed before the installation of the protective cover 4, thereby facilitating the ease with which a fastening tool is fit on the attachment screw 3 without sacrificing the ease of installation of the sensor body 2.

The protective cover 4 is equipped with the hooks 41 fit on the large-diameter portion (i.e., the tool engaging portion 32), thereby facilitating the ease with which the protective cover 4 is attached to or removed from the attachment screw 3.

As apparent from the above discussion, the gas sensor 1 has a structure in which the sensor body 2 is firmly secured to the sensor-mounting member 7 using the attachment screw 3 and which achieves firm installation of the protective cover 4.

Second Embodiment

Figure 7:
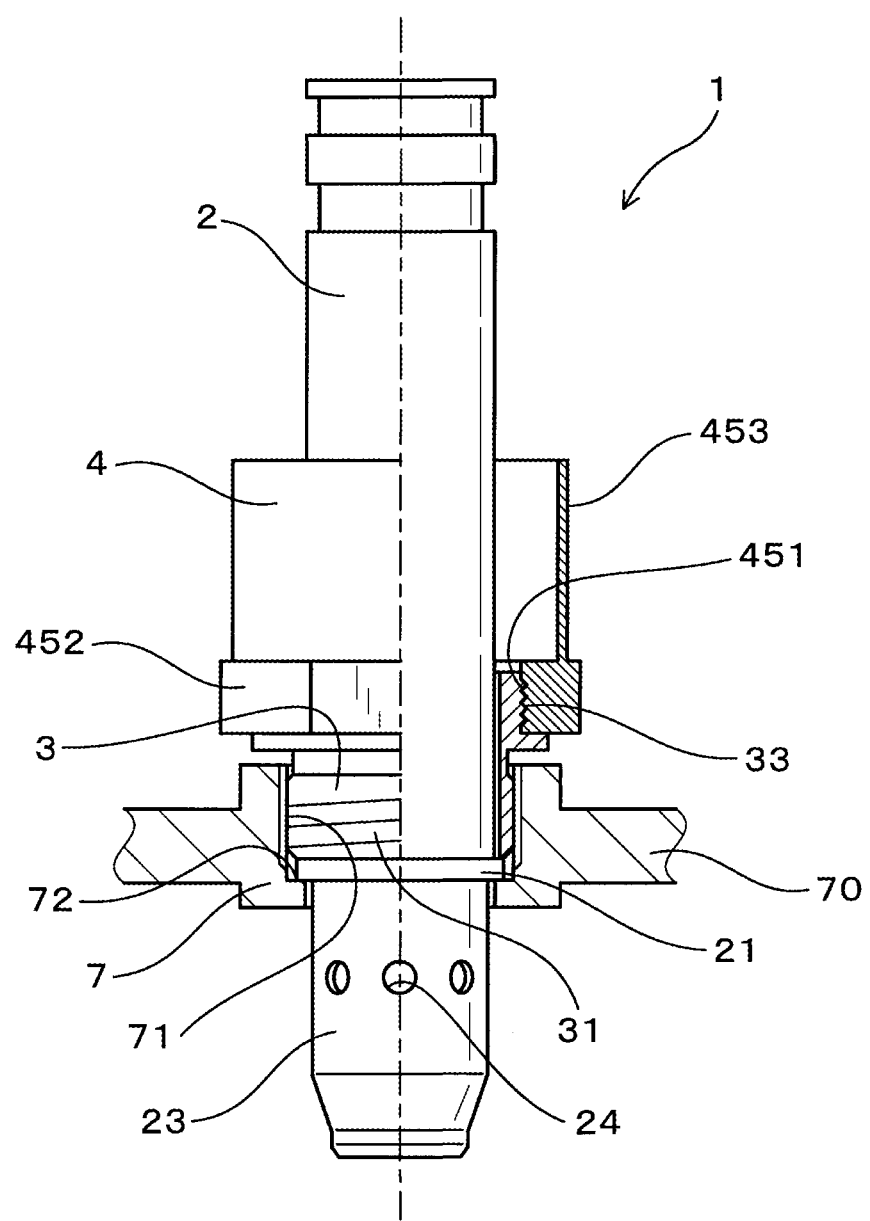
FIG. 7 is a partially sectional front view which illustrates a gas sensor secured to a mounting portion in the second embodiment.

The gas sensor 1 of this embodiment, as illustrated in FIG. 7, has the protective cover 4 threadably fit on the attachment screw 3.

Specifically, the attachment screw 3 has the base end side external thread 33 formed on an outer periphery of a base end portion thereof. The protective cover 4 has the internal thread 451 formed on an inner surface of a front end portion thereof. The securement of the protective cover 4 to the attachment screw 3 is achieved by threadable engagement between the internal thread 451 and the base end side external thread 33.

The protective cover 4 has the tool engaging portion 452 outside the circumference of the internal thread 451. The tool engaging portion 452 is substantially of, for example, a regular hexagonal shape, as viewed in the axial direction. The protective cover 4 also has the cylindrical portion 453 which extends from the base end of the tool engaging portion 452 toward the base end side of the gas sensor 1 parallel to the axial direction of the gas sensor 1.

The securement of the gas sensor 1 of this embodiment to the sensor-mounting member 7 is achieved in the following steps.

First, the protective cover 4 is threadably fastened to the attachment screw 3 mounted on the sensor body 2. Subsequently, the gas sensor 1 in which the sensor body 2, the attachment screw 3, and the protective cover 4 are assembled together is placed in the sensor-mounting member 7. The attachment screw 3 is then placed to engage the external thread 31 with the internal thread 71. A tool is then fitted on the tool engaging portion 452 of the protective cover 4 to turn the protective cover 4 in the circumferential direction, thereby achieving engagement of the internal thread 451 of the protective cover 4 with the base end side external thread 33 of the attachment screw 3 and also achieving engagement of the external thread 31 of the attachment screw 3 with the internal thread 71 of the sensor-mounting member 7. This results in firm securement of the protective cover 4 to the attachment screw 3 and also results in firm securement of the sensor body 2 to the sensor-mounting member 7 through the attachment screw 3. This provides an installation structure in which the gas sensor 1 is installed in the sensor-mounting member 7.

Other arrangements are identical with those in the first embodiment. In the second and following embodiments and their drawings, the same reference numbers as employed in the first embodiment refer to the same parts unless otherwise specified.

This embodiment also facilitates the ease with which the protective cover 4 is attached to or removed from the attachment screw 3 and offers the same beneficial advantages as those in the first embodiment.

Third Embodiment

Figure 8:
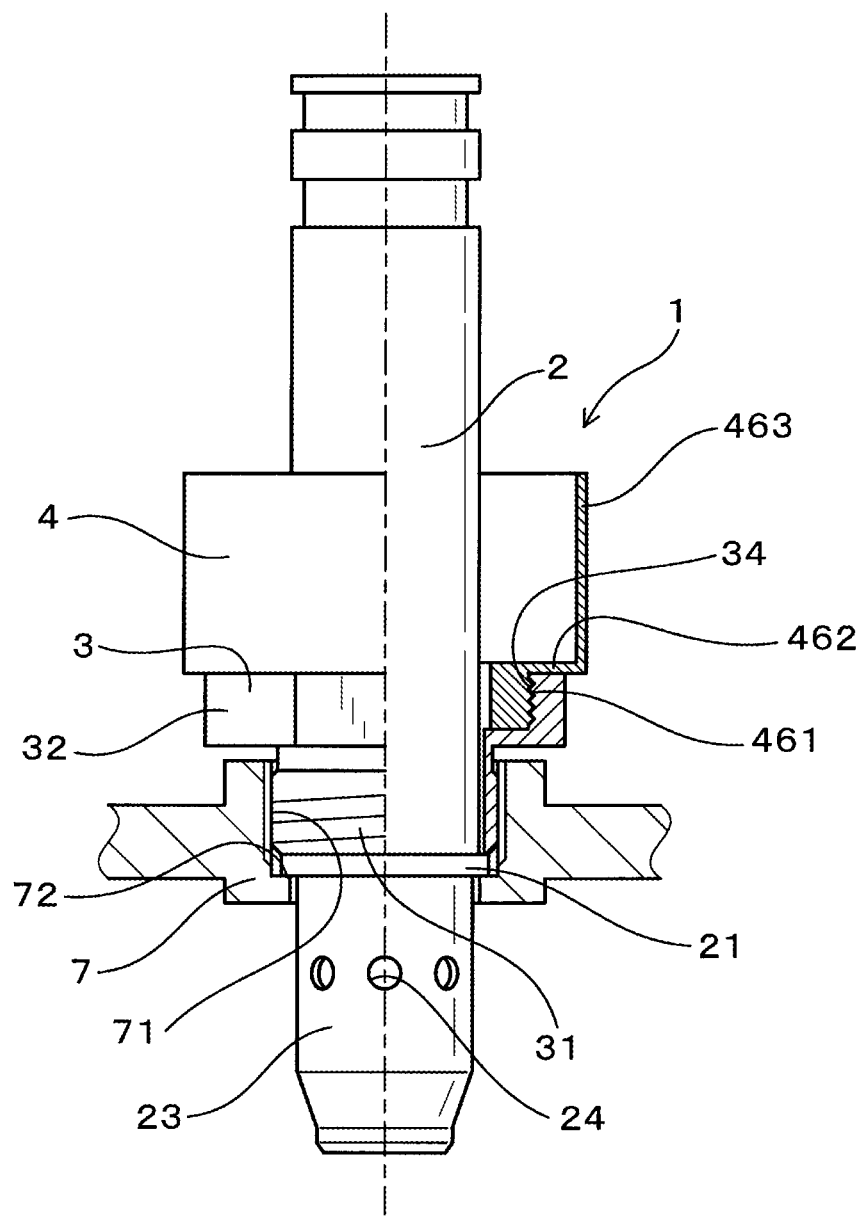
FIG. 8 is a partially sectional front view which illustrates a gas sensor secured to a mounting portion in the third embodiment.

This embodiment, as illustrated in FIG. 8, has the external thread 461 formed on the front end portion of the protective cover 4 and the external thread 34 formed on the base end portion of the attachment screw 3.

Specifically, in this embodiment, a relation of engagement between the protective cover 4 and the attachment screw 3 is opposite that in the second embodiment.

In this embodiment, the tool engaging portion 32 is located outside the circumference of the internal thread 34 of the attachment screw 3. The protective cover 4 includes the bottom plate 462 which extends outwardly from the base end of the external thread 461 and the cylindrical portion 463 which extends from an outer edge of the bottom plate 462 toward the base end of the gas sensor 1 in the axial direction of the gas sensor 1.

The attachment of the gas sensor 1 of this embodiment to the sensor-mounting member 7 is achieved in the following steps.

First, the attachment screw 3 placed on the outer circumference of the sensor body 2 is fastened to the sensor-mounting member 7 to achieve firm securement of the sensor body 2 to the sensor-mounting member 7. Subsequently, the external thread 461 of the protective cover 4 is fastened to the internal thread 34 of the attachment screw 3, thereby attaching the protective cover 4 to the attachment screw 3. This provides an installation structure in which the gas sensor 1 with the protective cover 4 is installed in the sensor-mounting member 7.

Other arrangements are identical with those in the first embodiment.

This embodiment also facilitates the ease with which the protective cover 4 is attached to or removed from the attachment screw 3 and offers the same beneficial advantages as those in the first embodiment.

Fourth Embodiment

Figure 9:
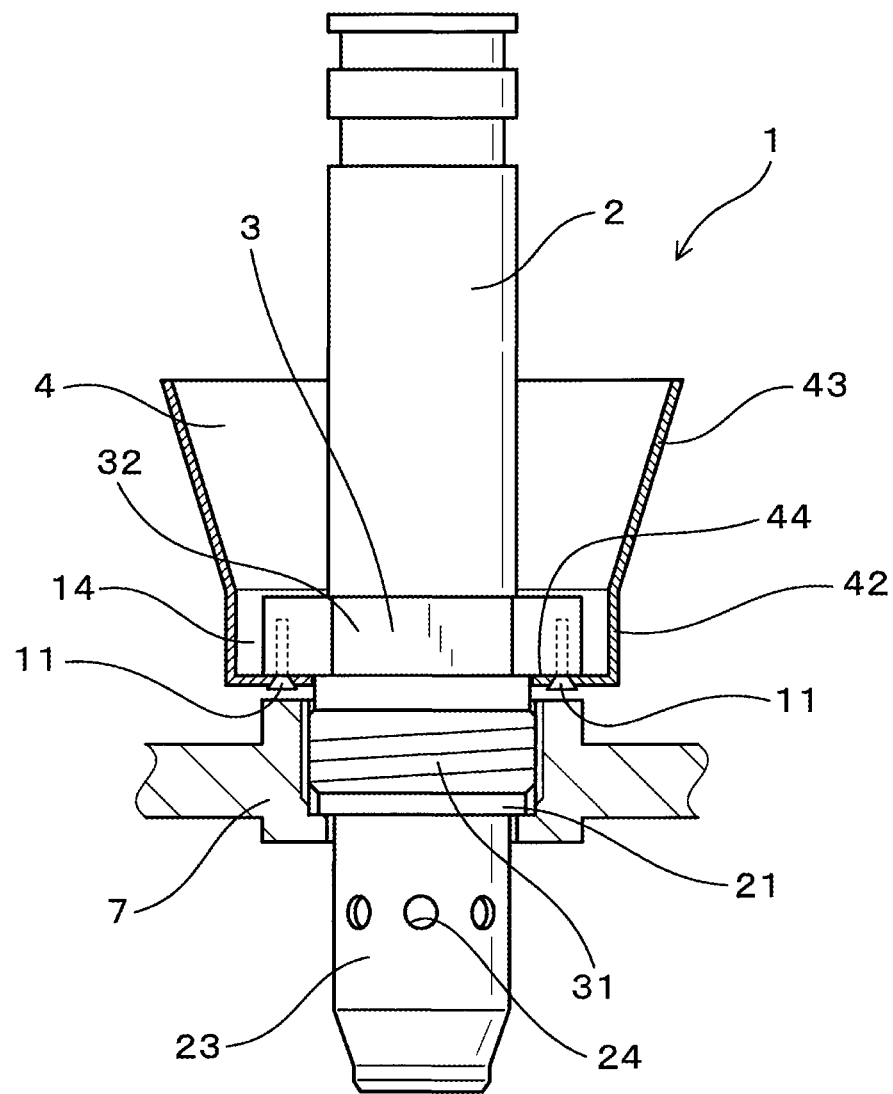
FIG. 9 is a partially sectional front view which illustrates a gas sensor secured to a mounting portion in the fourth embodiment.
Figure 10:
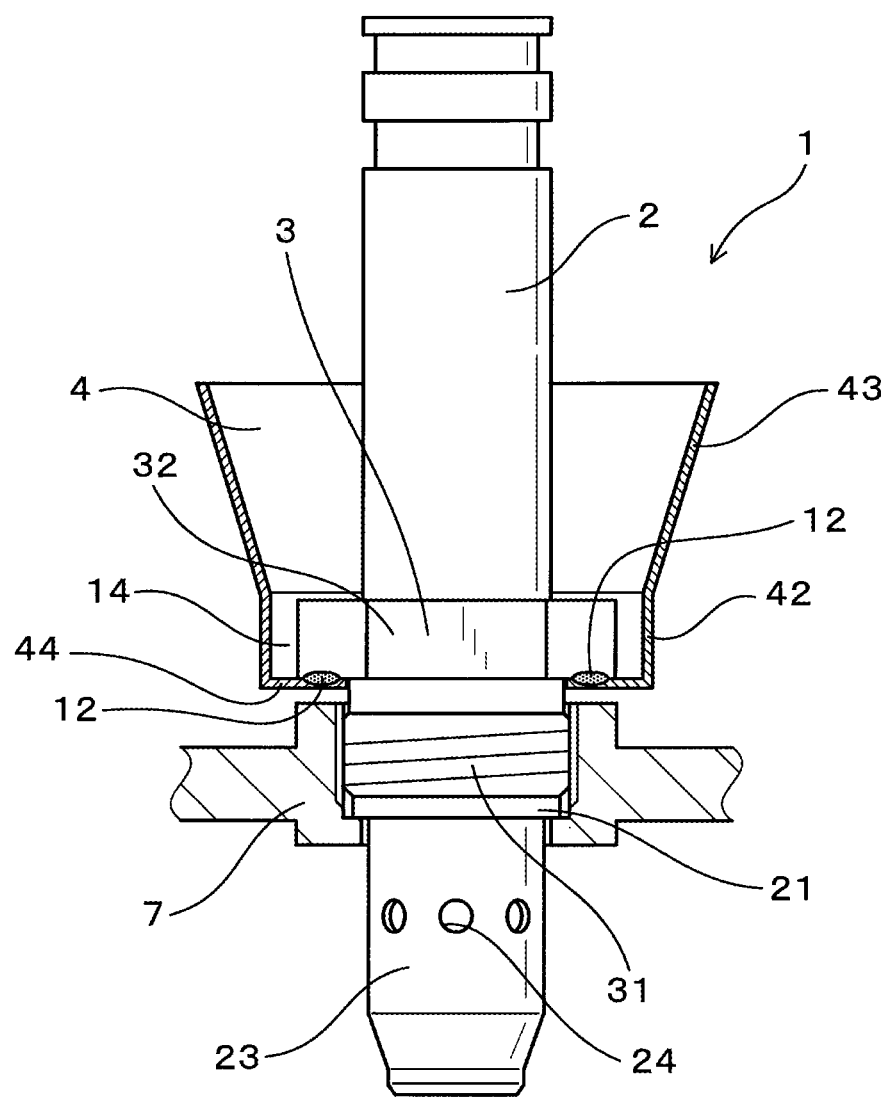
FIG. 10 is a partially sectional front view which illustrates another gas sensor secured to a mounting portion in the fourth embodiment.

The gas sensor 1 of this embodiment, as illustrated in FIGS. 9 and 10, has the protective cover 4 fixed on the attachment screw 3.

The gas sensor 1 shown in FIG. 9 has the protective cover 4 joined to the tool engaging portion 32 of the attachment screw 3 using screws or vises 11. Specifically, the joining of the protective cover 4 to the attachment screw 3 is achieved by fastening the vises 11 in the axial direction into an overlap between the bottom plate 44 of the protective cover 4 and the front end surface of the tool engaging portion 32.

The protective cover 4 may alternatively be, as illustrated in FIG. 10, welded to the tool engaging portion 32 of the attachment screw 3. Specifically, an overlap between the bottom plate 44 of the protective cover 4 and the front end surface of the tool engaging portion 32 is welded to join the attachment screw 3 and the protective cover 4 together. In FIG. 10, reference number 12 indicates a weld between the bottom plate 44 of the protective cover 4 and the front end surface of the tool engaging portion 32.

The gas sensor 1 of FIGS. 9 and 10 is required to secure the protective cover 4 to the attachment screw 3 before the sensor body 2 is firmly fixed in the sensor-mounting member 7 using the attachment screw 3. The air gap 14 is, therefore, provided between the tool engaging portion 32 of the attachment screw 3 and the cylindrical portion 42 of the protective cover 4 for insertion of a tool thereinto which is used in fastening the attachment screw 3.

The attachment of the protective cover 4 to the attachment screw 3 may be achieved in a way other than use of the vises 11 or the welding techniques as described above. A portion (s) of the attachment screw 3 to which the protective cover 4 is joined may be an outer surface or a base end surface of the tool engaging portion 32 as long as it is located closer to the base end side than the external thread 31 is.

This embodiment has the same other arrangements as in the first embodiment and offers the same beneficial advantages as in the first embodiment.

Fifth Embodiment

Figure 11:
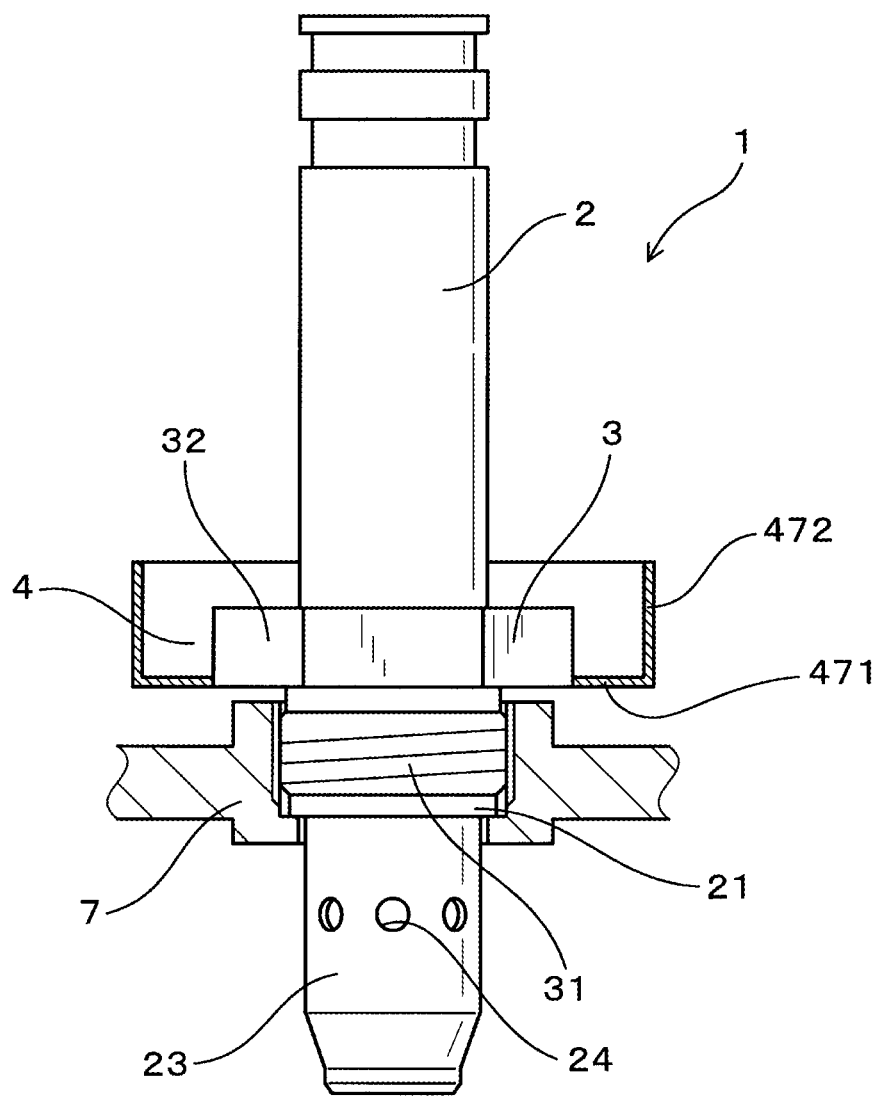
FIG. 11 is a partially sectional front view which illustrates a gas sensor secured to a mounting portion in the fifth embodiment.

The gas sensor 1 of this embodiment, as illustrated in FIG. 11, has the protective cover 4 formed integrally with the attachment screw 3.

Specifically, the protective cover 4 and the attachment screw 3 are made of a shaped one-piece member which includes the bottom plate 471 of the protective cover 4 which extends outwardly from the front end of the tool engaging portion 32 of the attachment screw 3 and the cylinder 472 which extends from an outer edge of the bottom plate 471 toward the base end side in the axial direction.

This embodiment has the same other arrangements as in the first embodiment and offers the same beneficial advantages as in the first embodiment.

Sixth Embodiment

The gas sensor 1 of this embodiment is different only in structure of the cylindrical portion 42 of the protective cover 4 from that of the first embodiment.

Figure 12:
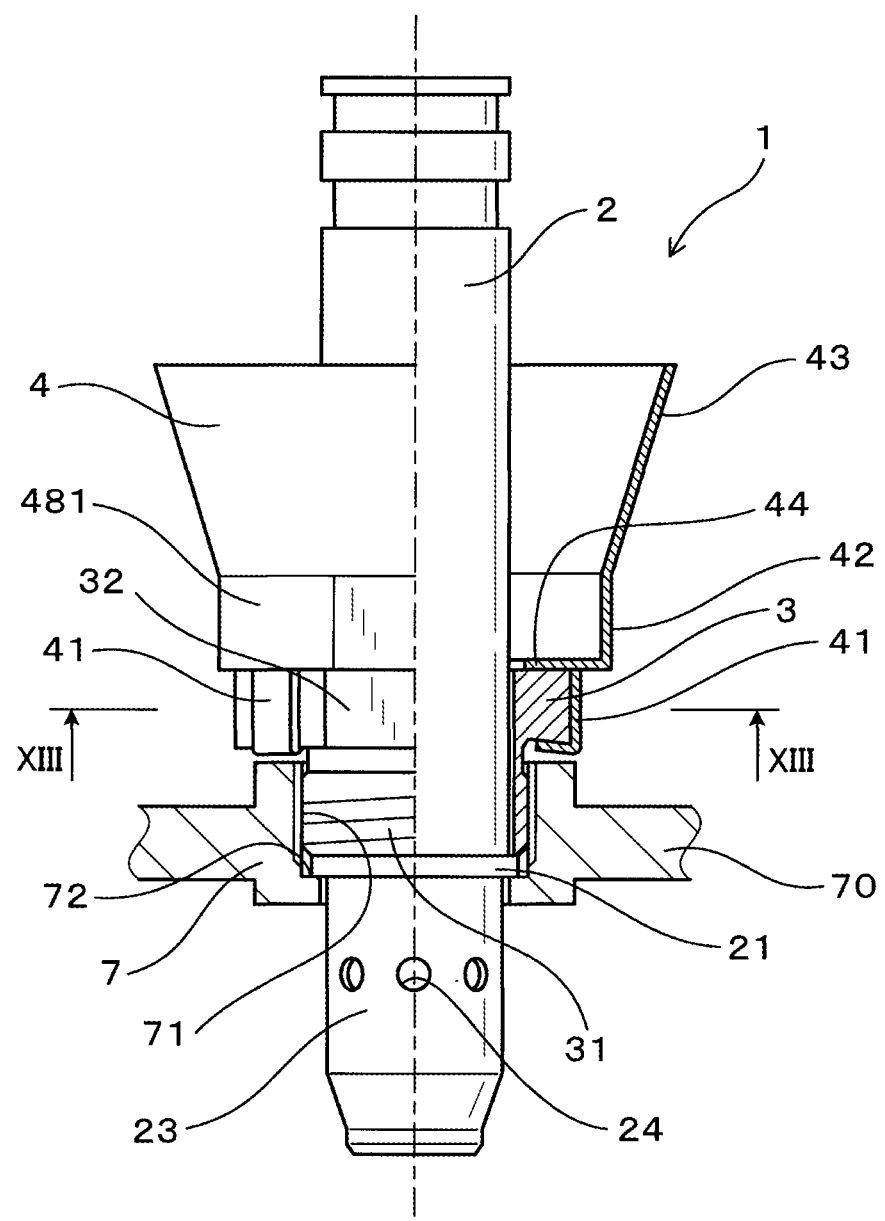
FIG. 12 is a partially sectional front view which illustrates a gas sensor secured to a mounting portion in the sixth embodiment.

The protective cover 4, as illustrated in FIG. 12, includes the hollow cylindrical portion 42 which extends parallel to the axial direction and, as clearly illustrated in FIG. 13, also has three pairs of planar surfaces on an outer circumference of the cylindrical portion 42. The planar surfaces of each pair extend parallel to each other. The cylindrical portion 42, like a hexagon bolt, has a substantially hexagonal axially-perpendicular transverse sectional area of the outer circumference thereof perpendicular to the axial direction. The outer circumference of the cylindrical portion 42 is used as the tool engaging portion 481 which a universal tool, such as a wrench or a spanner, is engageable. The outer circumference of the tool engaging portion 481 includes mutually parallel planar surfaces 482, mutually parallel planar surfaces 483, and mutually parallel planar surfaces 484. The term "axially-perpendicular transverse sectional area", as referred to herein, represents a sectional area extending perpendicular the axial direction of the gas sensor 1. The same applies to the following discussion.

This embodiment enables an universal tool to be fitted on one of the pairs of planar surfaces of the tool engaging portion 481 of the protective cover 4 secured to the attachment screw 3 and then rotated to turn the protective cover 4 in the circumferential direction thereof, thereby loosening the external thread 31 of the attachment screw 3 fixed on the protective cover 4 to be disengaged from the internal thread 71 of the sensor-mounting member 7. This causes the sensor 1 to be removed from the sensor-mounting member 7 without the need for removing the protective cover 4 from the attachment screw 3. This removal operation is more efficient than when the sensor 1 is removed from the sensor-mounting member 7 after the protective cover 4 is detached from the attachment screw 3 and also eliminates the need for special tools.

It is also possible to fit a universal tool on the outer periphery of the tool engaging portion 481 of the protective cover 4 when the gas sensor 1 in which the protective cover 4 has already been secured to the attachment screw 3 is mounted in the sensor-mounting member 7.

This embodiment has the same other arrangements as in the first embodiment and offers the same beneficial advantages as in the first embodiment.

Seventh Embodiment

The gas sensor 1 of this embodiment is a modification of the sixth embodiment.

The protective cover 4 is, as illustrated in FIG. 14, equipped with two pairs of mutually parallel planar surfaces formed on an outer circumference of the cylindrical portion 42. The cylindrical portion 42, like a square bolt, has a substantially square axially-perpendicular transverse sectional area of the outer circumference thereof perpendicular to the axial direction. The outer circumference of the cylindrical portion 42 is used as the tool engaging portion 491 which a universal tool, such as a wrench or a spanner, is engageable. The outer circumference of the tool engaging portion 491 includes mutually parallel planar surfaces 492 and mutually parallel planar surfaces 483.

This embodiment, like the sixth embodiment, enables the sensor 1 to be removed from the sensor-mounting member 7 without the need for removing the protective cover 4 from the attachment screw 3. This removal operation is efficient. The configuration of the outer circumference of the tool engaging portion 491 is useful in mounting the gas sensor 1 in the sensor-mounting member 7 without removing the protective cover 4 from the attachment screw 3.

This embodiment has the same other arrangements as in the first embodiment and offers the same beneficial advantages as in the first embodiment.

The protective cover 4 may be designed to have another shape in which the outer circumference of the cylindrical portion 42, like the sixth and seventh embodiment, has at least one pair of mutually parallel planar surfaces. The protective cover 4 may alternatively be designed to have the cylindrical portion 42 whose axially-perpendicular transverse sectional area of an outer circumference is in the form of a regular even-sided polygon. Specifically, the protective cover 4 has at least two pairs of mutually parallel planar surfaces formed on an outer circumference of the cylindrical portion 42. If the regular even-sided polygon is defined as a regular n-sided polygon (n is even more than or equal to four), the protective cover 4 will have (n+2) pairs of mutually parallel planar surfaces on the outer circumference of the cylindrical portion 42.

Eighth Embodiment

The gas sensor 1 of this embodiment is different from the first embodiment only in structure of the tool engaging portion 32 (i.e., the large-diameter portion) on the base end side of the attachment screw 3.

Figure 15:
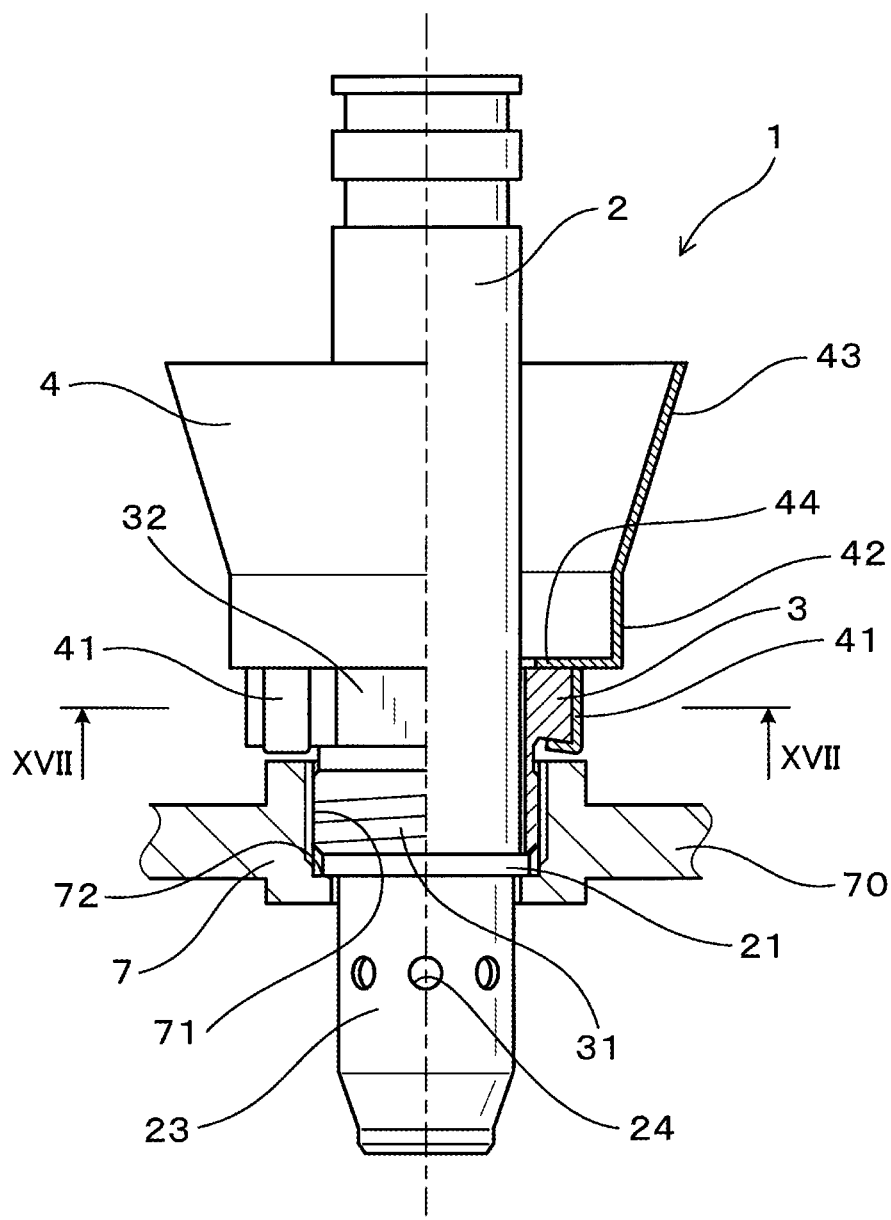
FIG. 15 is a partially sectional front view which illustrates a gas sensor secured to a mounting portion in the eighth embodiment.

The hooks 41 of the protective cover 4 are, as illustrated in FIG. 15, fit on the tool engaging portion 32.

The tool engaging portion 32 of this embodiment is, as can be seen in FIG. 16, like a hexagon bolt, and has a substantially regular hexagonal axially-perpendicular traverse sectional area of an outer circumference thereof. The attachment screw 3 has three pairs of mutually parallel planar surfaces on an outer circumference thereof. Specifically, the outer circumference of the tool engaging portion 32 includes mutually parallel planar surfaces 35, mutually parallel planar surfaces 36, and mutually parallel planar surfaces 37. Of the six outer circumferential surfaces of the tool engaging portion 32, three surfaces 35, 36, and 37 which obliquely face each other and are not located adjacent each other have grooves 38 which are recessed inwardly in the radial direction of the tool engaging portion 32 and in which the hooks 41 of the protective cover 4 are fit. The grooves 38 have a width which is substantially identical with or slightly greater than that of the hooks 41 for facilitating the fitting of the hooks 41.

The hooks 41 of the protective cover 4 are, as illustrated in FIG. 17, fit in the grooves 38 to achieve firm engagement with the tool engaging portion 32. The tool engaging portion 32 and the protective cover 4 are shaped to have the hooks 41 which do not protrude outside the outer circumference of the tool engaging portion 32 in the radial direction when the hooks 41 are fit in the grooves 38. For realizing this structure, for example, the grooves 38 are designed to have a depth in the radial direction which is substantially identical with or greater than the thickness of the hooks 41.

When the hooks 41 of the protective cover 4 are fit in the grooves 38 of the tool engaging portion 32 of the attachment screw 3, the hooks 41 do not protrude outside the outer circumference of the tool engaging portion 32 in the radial direction. This enables a universal tool, such as a spanner, to be fit on one of the pairs of the outer surfaces of the tool engaging portion 32 and be rotated without any physical interference of the hooks 41 in the grooves 38 with the fitting of the universal tool on the tool engaging portion 32. The disengagement of the external thread 31 of the attachment screw 3 from the internal thread 71 of the sensor-mounting member 7 is, thus, achieved by turning the attachment screw 3 in the circumferential direction thereof, thereby accomplishing the removal of the gas sensor 1 from the sensor-mounting member 7 without the need for detaching the protective cover 4 from the attachment screw 3. Such a removal operation is more efficient than when the sensor 1 is removed from the sensor-mounting member 7 after the protective cover 4 is detached from the attachment screw 3 and also eliminates the need for special tools.

Like the sixth and seventh embodiment, the configuration of the outer circumference of the tool engaging portion 32 is useful in mounting the gas sensor 1 in the sensor-mounting member 7 without removing the protective cover 4 from the attachment screw 3.

This embodiment has the same other arrangements as in the first embodiment and offers the same beneficial advantages as in the first embodiment.

The attachment screw 3 may be designed to have the tool engaging portion 32 whose axially-perpendicular transverse sectional area of an outer circumference is in the form of a regular even-sided polygon. Specifically, the tool engaging portion 32 has at least two pairs of mutually parallel planar surfaces formed on the outer circumference thereof. The tool engaging portion 32 has the grooves 38 which are recessed from some or all of side surfaces of the regular even-sided polygonal circumference thereof in the radial direction and in which the hooks 41 are fit. In a case where the grooves 38 are formed in the all side surfaces of the regular even-sided polygonal circumference, for example, the planar surfaces 35, 36, and 37 in FIG. 16 all have the grooves 38. Alternatively, in a case where the grooves 38 are formed in some of the side surfaces of the regular even-sided polygonal circumference, the tool engaging portion 32 may have the grooves 38 formed in each pair of mutually parallel planar surfaces.

The above eighth embodiment may alternatively designed to have a combination of the sixth and seventh embodiments. Such a structure enables a universal tool to be fit on either of the attachment screw 3 or the protective cover 4 for removing the gas sensor 1 from the sensor-mounting member 7.

Comparative Example

Figure 18:
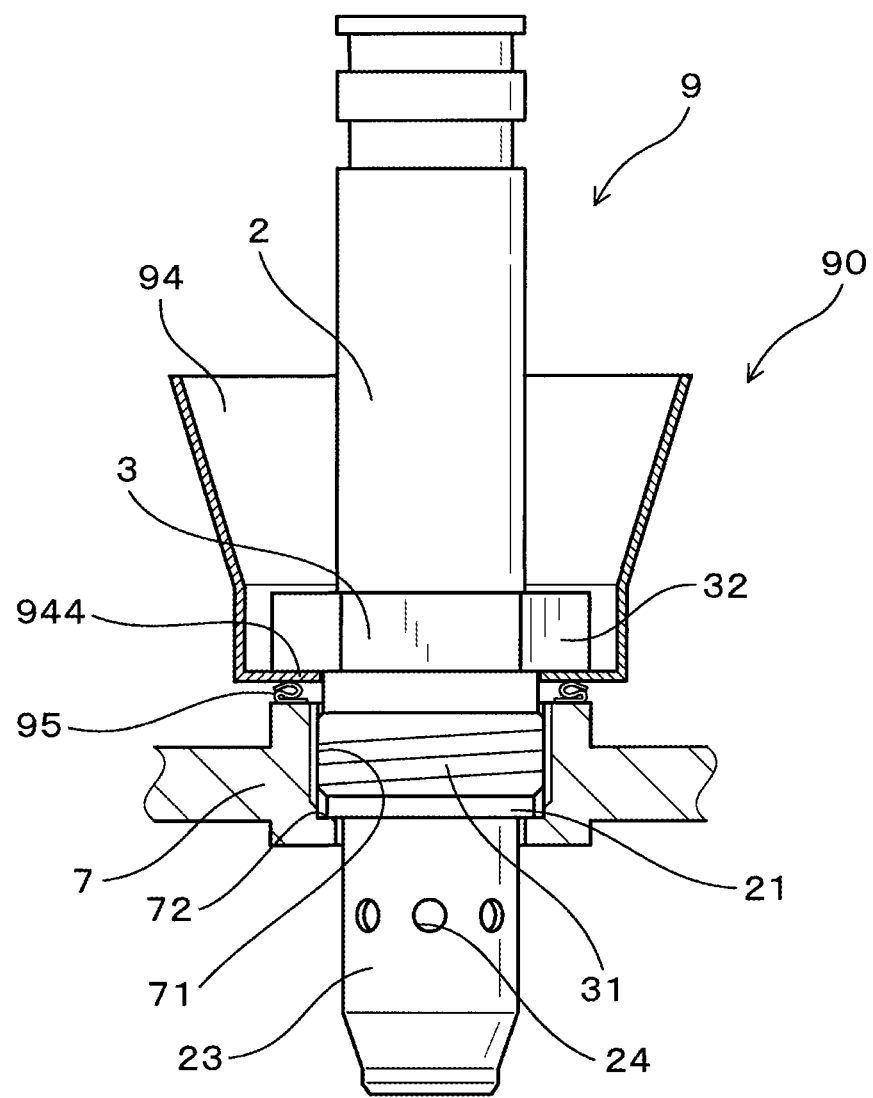
FIG. 18 is a partially sectional front view which illustrates a gas sensor secured to a mounting portion in a comparative example.

This example, as illustrated in FIG. 18, has the gas sensor mounting mechanism 90 which holds the bottom plate 944 of the protective cover 94 between the tool engaging portion 32 of the attachment screw 3 and the sensor-mounting member 7 to place the protective cover 94 around the gas sensor 9. The reference numbers used in this embodiment refer to the same parts as those in the first embodiment unless otherwise specified.

The annular gasket 95 is interposed between the bottom plate 944 and the sensor-mounting member 7.

The attachment screw 3 is disposed on the sensor body 2 of the gas sensor 9 to be rotatable in the same way as in the first embodiment.

This example is designed to have the flange 21 of the sensor body 2 held between the bearing surface 72 of the sensor-mounting member 7 and the front end surface of the attachment screw 3 in the axial direction to secure the sensor body 2 to the sensor-mounting member 7. The protective cover 94 has the bottom plate 944 retained between the tool engaging portion 32 of the attachment screw 3 and the sensor-mounting member 7 through the gasket 95, thereby achieving a joint between itself and the sensor-mounting member 7.

The protective cover 94 and the sensor body 2 are, therefore, fastened to the sensor-mounting member 7 through different portions of the attachment screw 3. Specifically, the protective cover 94 is retained between the front end surface of the tool engaging portion 32 of the attachment screw 3 and the base end surface of the sensor-mounting member 7, while the sensor body 2 is retained between the front end surface of the attachment screw 3 and the bearing surface 72 of the sensor-mounting member 7.

It, therefore, becomes difficult to fasten both the protective cover 94 and the sensor body 2 with a sufficient degree of fixing power. Specifically, increasing in power to fasten the protective cover 94 will result in a decrease in power to fasten the sensor body 2, while increasing in power to fasten the sensor body 2 will result in a decrease in power to fasten the protective cover 94.

The above comparative example in which the sensor body is secured to the sensor-mounting member using the attachment screw, therefore, has room for improvement.

In contrast, the gas sensor 1 has a structure which uses the attachment screw 3 to secure the sensor body 2 to the sensor-mounting member 7 to achieve a firm joint of the protective cover 4 to the sensor body 2.

The present invention is not limited to the above embodiments, but may be modified in various ways. For instance, the configuration of the protective cover equipped with large-diameter portion 43 of the first embodiment may be used in the second, third, or fifth embodiment. The first embodiment may alternatively be designed to have another shape of the protective cover which is not equipped with the large-diameter portion 43 and in which the cylindrical portion 42 has a constant diameter and extends straight toward the base end side without the large-diameter portion 43.

The invention claimed is:

1. A gas sensor which comprises a sensor body in which a sensor device is disposed and a cylindrical attachment screw disposed on an outer circumference of the sensor body to be rotatable, the gas sensor being designed to be secured to a mounting portion equipped with an internal thread engaging the attachment screw and a bearing surface which is located on a front end side of the internal thread, wherein the sensor body has a flange which protrudes outwardly on a front end side of the attachment screw, the flange being designed to be retained between the bearing surface of the mounting portion and the attachment screw in an axial direction, and in that a protective cover is directly secured to the attachment screw closer to a base end side than an external thread engaging the internal thread is and covers an outer periphery of at least a portion of the sensor body which is arranged closer to the base end side than the mounting portion is.

2. A gas sensor as set forth in claim 1, wherein the protective cover is secured to the attachment screw to be detachable therefrom.

3. A gas sensor as set forth in claim 1, wherein the attachment screw has a large-diameter portion which protrudes outwardly outside the external thread on a base end side of the external thread and in that the protective cover is equipped with hooks fit on the large-diameter portion.

4. A gas sensor as set forth in claim 3, wherein the large-diameter portion has an axially-perpendicular transverse sectional area of an outer circumference thereof which is in a form of a regular even-sided polygon and also has grooves which are recessed from a plurality of sides of the regular even-sided polygon inwardly in a radial direction thereof and in which the hooks are fit and in that the hooks are designed not to protrude from the outer circumference of the large-diameter portion outwardly in a circumferential direction when the hooks are fit in the grooves.

5. A gas sensor as set forth in claim 1, wherein the protective cover has a cylindrical portion extending parallel to the axial direction and also has at least one pair of mutually parallel planar surfaces on an outer circumference of the cylindrical portion.

6. A gas sensor as set forth in claim 5, wherein the protective cover has the cylindrical portion whose axially-perpendicular transverse sectional area of the outer circumference thereof is in the form of a regular even-sided polygon.

7. A gas sensor as set forth in claim 1, wherein the gas sensor further comprises leads extending outside the base end side of the gas sensor.

8. A gas sensor as set forth in claim 1, wherein the gas sensor further comprises a device cover having gas holes which are configured to receive a gas and which are positioned closer to the front end side than the base end side of the gas sensor.

9. A gas sensor as set forth in claim 1, wherein the protective cover is detachably mounted directly on the attachment screw.

* * * * *